United States Patent [19]

Weigert

[11] 4,254,061
[45] Mar. 3, 1981

[54] PREPARATION OF MONOMETHYLAMINE

[75] Inventor: Frank J. Weigert, Wilmington, Del.

[73] Assignee: E. I. Du Pont de Nemours and Company, Wilmington, Del.

[21] Appl. No.: 74,418

[22] Filed: Sep. 11, 1979

[51] Int. Cl.$^3$ .............................................. C07C 85/06
[52] U.S. Cl. .................................... 564/479; 564/480
[58] Field of Search ........................... 260/583 J, 585 B

[56] References Cited

U.S. PATENT DOCUMENTS

| | | | |
|---|---|---|---|
| 1,875,747 | 9/1932 | Martin | 260/585 B |
| 2,012,333 | 8/1935 | Arnold | 260/585 B X |
| 2,092,431 | 9/1937 | Swallen et al. | 260/583 J X |
| 2,113,241 | 4/1938 | Punnett | 260/585 B |
| 4,082,805 | 4/1978 | Kaeding | 252/455 Z X |

*Primary Examiner*—John Doll

[57] ABSTRACT

Catalytic process for producing monomethylamine from methanol and ammonia, said process comprising reacting methanol and ammonia, in such amounts so as to provide a C/N ratio, from the methanol and ammonia reactants, of 0.5–1.5, over the catalyst selected from (a) mordenite wherein the primary cation is Li, Na, HNa having at least 2% Na by weight, K, Ca, Sr, Ba, Ce, Zn or Cr
(b) ferrierite wherein the primary metal cation is Li, Na, K, Ca, Sr, Ba, Ce or Fe
(c) erionite ore
(d) calcium erionite and
(e) clinoptilolite ore, at a temperature of 250°–475° C. and a pressure of 7–7000 kPa, a contact time, normalized to 7 kPa, of 0.1 to 60 seconds and a methanol conversion of 15–95%.

8 Claims, 3 Drawing Figures

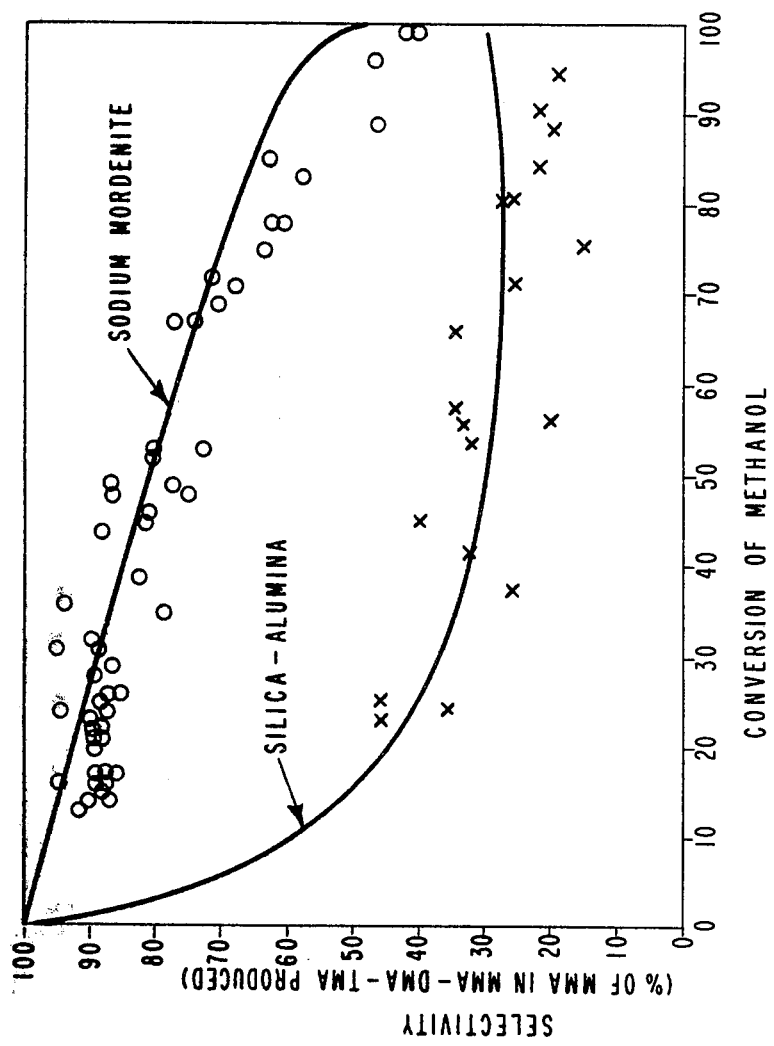

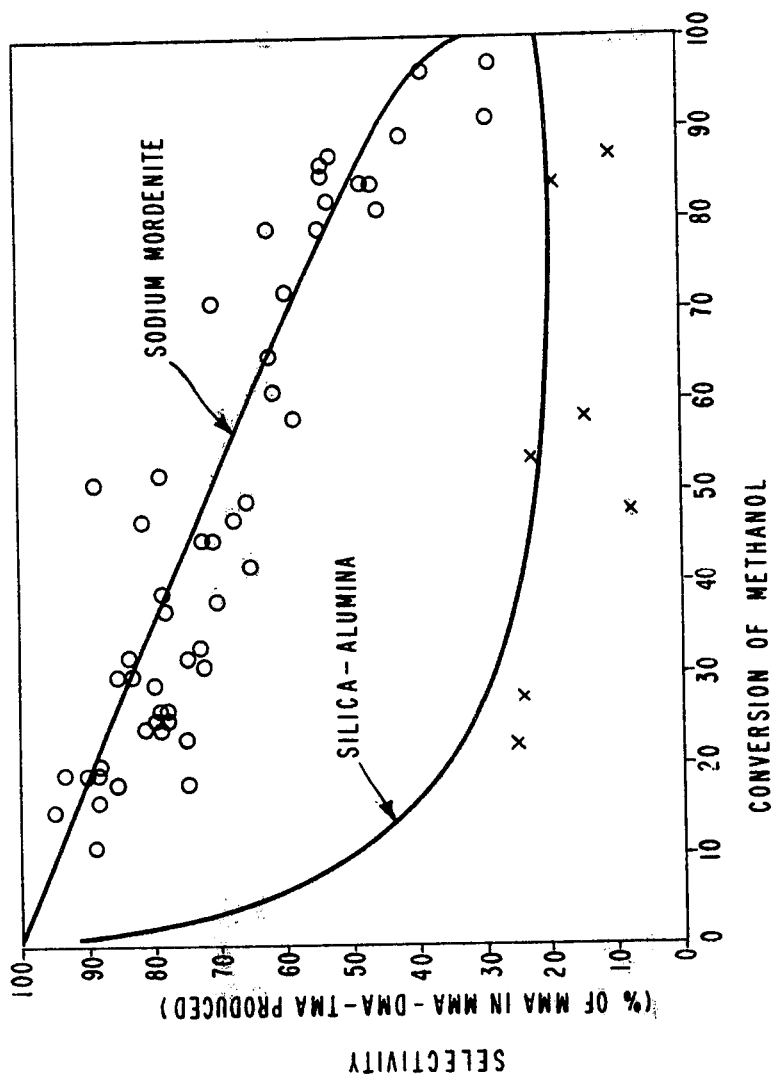

PREPARATION OF MONOMETHYLAMINE

DESCRIPTION

1. Technical Field

This invention relates to the preparation of monomethylamine by a catalytic process from methanol and ammonia.

2. Background

It is well known in the art that the catalyzed reaction of methanol and ammonia can be employed to produce mono-, di- and/or trimethylamine. To facilitate the formation of any one of the methylamines various expedients can be used. For example, it is known that the use of dimethyl ether in conjunction with or in place of methanol, recycling unwanted methylamines, the use of varying molar ratios of the reactants and the use of specific dehydrating or aminating catalysts can be employed to alter the relative amounts of the various amines in the product.

Exemplary, but not intended to be all inclusive, of such art, U.S. Pat. No. 3,278,598 discloses an improved, Raney nickel-catalyzed, liquid phase process of reacting primary and secondary alcohols and ammonia, the improvement comprising the use of a rhodium, palladium or ruthenium cocatalyst, to provide increased formation of secondary amine. Similarly, U.S. Pat. No. 3,387,032 discloses a catalytic process for providing increased amounts of dimethylamine from methanol and/or dimethyl ether and ammonia, using as the catalyst a silica gel-based alumina which has been partially steam deactivated and then impregnated with silver phosphate rhenium heptasulfide, molybdenum sulfide or cobalt sulfide. U.S. Pat. Nos. 2,394,515 and 2,394,516 disclose catalytic processes for preparing polyalkylamines, with lesser quantities of the monoalkylamine, from an alcohol and/or ether of 1-5 carbon atoms and ammonia, using as the catalyst an aluminum oxide or salt which has been coated, first with silica and then with a vanadium salt or molybdenum oxide. The related U.S. Pat. No. 2,349,222 utilizes as the catalyst a granular alumina which has been coated with a nickel, cobalt or chromium oxide hydrogenation/dehydrogenation catalyst. U.S. Pat. No. 2,456,559 discloses that higher amounts of mono- and dimethylamine, and a reduced amount of trimethylamine, can be achieved in the catalyzed process wherein water is introduced along with the methanol and ammonia. U.S. Pat. No. 1,799,722 and U.S. Pat. No. Re. 19,632 disclose catalytic processes wherein trimethylamine is introduced with the methanol and ammonia to suppress the formation of trimethylamine and provide increased amounts of dimethylamine. U.S. Pat. No. 1,992,935 discloses a catalytic process for preparing a mixture of primary, secondary and tertiary methylamines, principally dimethylamine, from methanol and ammonia, using as the catalyst a dehydrating oxide supported on a porous rigid gel such as silica gel. British Pat. No. 422,563 discloses a catalytic process for producing secondary amine by employing the primary amine as starting material in addition to ammonia and alcohol.

Restelli et al. in A.I.Ch.E. Journal, Vol. 12, No. 2, 292-296, March, 1966, describe studies of transmethylation reactions of monomethylamine and dimethylamine over montmorillonite, a hydrated magnesium/calcium oxide-containing aluminosilicate. With the reactions being carried out at about 320°-371° C., at low conversions the monomethylamine is converted to dimethylamine, the rate being directly proportional to the amine partial pressure, thus indicating that adsorption of monomethylamine on the catalyst surface is rate-determining.

U.S. Pat. No. 3,384,667 discloses a process for producing monosubstituted and disubstituted amines, in preference to trisubstituted amines, by reacting an alcohol and ammonia over a dehydrated crystalline metal aluminosilicate catalyst having pores of a diameter that pass the monosubstituted and disubstituted amine products but not the trisubstituted amine products. The related U.S. Pat. No. 4,082,805 discloses a process for producing primary aliphatic amines, in preference to secondary and tertiary amines, from a $C_1$-$C_5$ alcohol or ether and ammonia over a natural or synthetic dehydrated crystalline aluminosilicate having the structure of ZSM-5, ZSM-11 or ZSM-21, at 300°-500° C., at one atmosphere to 1000 psig pressure, the feed rate of alcohol or ether and ammonia being within the ratio 1:1 to 5:1.

Methylamines presently are generally produced commercially by a continuous process for methanol and ammonia, using an amorphous silica-alumina catalyst. Even at low methanol conversions such processes generally produce more trimethylamine than mono- and dimethylamine. Production of the maximum amount of monomethylamine is achieved when equilibrium is reached, at high methanol conversion. However, the relative amounts of the three amines produced at equilibrium depend, to a large extent, on the carbon/nitrogen (C/N) ratio, that is, the methanol/ammonia ratio in the reactants. At carbon/nitrogen ratios of about one the product mixture contains, on a mole basis, about 55% ammonia, 22% trimethylamine (TMA), 12% monomethylamine (MMA) and 12% dimethylamine (DMA). The product mixture can be separated and the less desirable methylamine can be recycled.

Monomethylamine is employed in the manufacture of: pharmaceutical intermediates for the xanthine alkaloids, theophylline, caffeine, the symphatomimetic drugs such as ephedrine and the analgesic meperidine; surface active agents; photographic developers; dyes; and soil fumigants, fungicides and insecticides for agriculture.

An object of this invention, therefore, is to provide a process for selectively preparing monomethylamine directly from methanol and ammonia, which process minimizes the formation of dimethylamine and trimethylamine. Other objects will become apparent hereinafter.

BRIEF DESCRIPTION OF DRAWINGS

The accompanying drawings form a material part of this disclosure.

FIGS. 2 and 3 provide plots showing the selectivity of the catalyst of the invention process, as compared to the use of a conventional amorphous silica-alumina catalyst which is outside the invention, in preparing monomethylamine from methanol and ammonia at two different C/N feed ratios.

Figure 1:
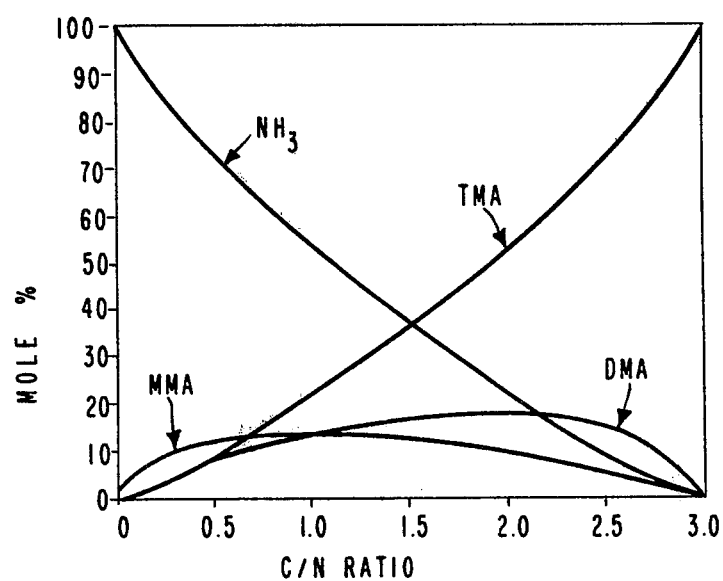
FIG. 1 provides plots showing the equilibrium distribution of ammonia, monomethylamine, dimethylamine and trimethylamine at various C/N ratios (0 to 3.0).

More specifically, the drawings provide plots showing the percentages of monomethylamine in the monomethylamine/dimethylamine/trimethylamine products obtained at varying conversions of methanol with the aforesaid catalysts.

DISCLOSURE OF INVENTION

For further comprehension of the invention, and of the objects and advantages thereof, reference may be made to the following description and accompanying drawings and to the appended claims in which the various novel features of the invention are not particularly set forth.

The invention herein resides in an improved catalytic process, for example, over those of U.S. Pat. Nos. 4,082,805 and 3,384,667, for preparing monomethylamine from methanol and ammonia. More specifically, the invention resides in the catalytic process, which can be carried out continuously, wherein methanol and ammonia, in such amounts so as to provide a carbon/nirogen (C/N) ratio, from the methanol and ammonia reactants, of 0.5 to 1.5, are reacted over a dehydrated crystalline aluminosilicate (Zeolite) catalyst selected from (a) mordenite wherein the primary cation is Li, Na, HNa having at least 2% Na by weight (for example, 2-4.3% Na), K, Ca, Sr, Ba, Ce, Zn or Cr
(b) ferrierite wherein the primary metal cation is Li, Na, K, Ca, Sr, Ba, Ce or Fe
(c) erionite ore
(d) calcium erionite and
(e) clinoptilolite ore, at a temperature of 250°-475° C., a pressure of 1-1000 psi (7-7000 kPa), a contact time, normalized to 7 kPa pressure, of 0.1-60 seconds and a methanol conversion of 15-95%. Preferably, the process is carried out with the Na or HNa mordenite catalyst at 350°-400° C. and 10-500 psi (70-3000 kPa), especially 300 psi (2000 kPa), at a contact time of 1-10 seconds. The preferred catalysts herein are sodium mordenite because it provides good selectivity and the HNa mordenite because it provides both a high reaction rate and good selectivity. Use of the term "HNa" in the description of mordenite is intended to indicate the presence of both $H^+$ and $Na^+$ cations.

Table I shows relative rate constants derived for the seven types of reactions commonly involved in methylamine production from methanol and ammonia, using three conventional catalysts and the catalysts of the process of this invention, the latter being exemplified in this instance by sodium mordenite. For each catalyst type the rates are relative to that of reaction (1) arbitrarily selected as 1 (written as ≡1).

TABLE I

| Equation | Sodium Mordenite | Amorphous Silica-Alumina | $Al_2O_3$ | REX* |
|---|---|---|---|---|
| (1) $NH_3 + MeOH \rightarrow MMA + H_2O$ | ≡1 | ≡1 | ≡1 | ≡1 |
| (2) $MMA + MeOH \rightarrow DMA + H_2O$ | 0.7 | 20 | 15 | >100 |
| (3) $DMA + MeOH \rightarrow TMA + H_2O$ | 0.5 | 120 | 45 | >10,000 |
| (4) $MMA + MMA \rightarrow DMA + NH_3$ | 0.09 | 4 | ** | ** |
| (5) $DMA + DMA \rightarrow TMA + MMA$ | 0.0022 | 7.2 | ** | ** |
| (6) $MMA + DMA \rightarrow TMA + NH_3$ | 0.045 | 20.4 | ** | ** |
| (7) $MeOH + MeOH \rightarrow DME + H_2O$ | <0.01 | ~1 | >>1 | ~1 |

TABLE I-continued

| Equation | Sodium Mordenite | Amorphous Silica-Alumina | $Al_2O_3$ | REX* |
|---|---|---|---|---|

*REX = Rare Earth X Zeolite
**In the same ratios as on amorphous silica-alumina for reactions (4), (5) and (6).
< = less than
> = greater than
>> = much greater than
~ = about From the table it may be seen that the rate of each of the undesirable reactions (2) through (7) is substantially less when the catalyst of the invention process is used.

Most of the catalysts which are useful herein are commonly available or can be prepared readily by one skilled in the art. Following are examples of preparative procedures which can be employed.

Sodium-hydrogen mordenite can be prepared by admixing sodium mordenite extrusions and aqueous hydrochloric acid, in appropriate amounts, allowing the mixture to stand overnight, removing the solids by filtration, washing the recovered solids with distilled water, and then air drying and calcining the solids at 400° C. for four hours.

Calcium mordenite can be prepared by refluxing an aqueous calcium chloride solution (25 grams of calcium chloride in 150 ml of distilled water) containing 20 grams of sodium mordenite for three days, decanting the supernatant, adding fresh aqueous calcium chloride solution, refluxing another three days, removing the solids by filtration, washing the recovered solids with distilled water to remove chloride, and then air drying and calcining the solids.

Calcium erionite can be prepared by refluxing an aqueous calcium chloride solution containing erionite ore for several hours, decanting the supernatant, and washing the recovered solids with water to remove chloride.

Other crystalline aluminosilicates (Zeolites) such as strontium, barium or cerium mordenite and calcium, strontium, barium or cerium ferrierite can be prepared by refluxing 10 grams of the appropriate Zeolite and 10 grams of the nitrate salt in 100 ml of water, removing the solids by filtration, washing the recovered solids with distilled water, and then drying the solids for two hours at 110° C., two hours at 200° C. and 4 hours at 400° C.

Process variables of this invention include methanol/ammonia (C/N) ratio, temperature, pressure and contact time (flow rate). If the temperature is too low, the conversion of methanol and ammonia to monomethylamine will be low. If the temperature is too high, equilibration and coking (carbonization) may result unless the contact time is reduced. Unduly large reaction vessels are required if the process is carried out at very low pressure, and the products must be refrigerated to condense them for further purification; costly thick-walled vessels are required at excessively high pressures. Short contact times result in low methanol-ammonia conversions and long contact times may result either in inefficient use of catalyst at low temperatures, or equilibration and coking at high temperatures. Generally, contact times of 0.1-60 seconds, normalized to 7 kPa pressure, are satisfactory, with 1-10 seconds being preferred (corresponding to flow rates of 0.04-25 g of methanol/g of catalyst/hour, preferably 0.25–2.5 g of methanol/g of catalyst/hour).

The reactant ratio of methanol and ammonia (the C/N ratio) is vitally important, as can be seen from FIG. 1 which illustrates the effect of the C/N ratio on the ammonia-amine distribution at equilibrium. At a low C/N ratio, for example, less than about 0.5, monomethylamine is favored regardless of the catalyst employed. As the C/N ratio increases, production of trimethylamine increases sharply but the amounts of monomethylamine and dimethylamine produced change to a lesser degree, decreasing to zero at a C/N ratio of 3.0, as the trimethylamine production reaches 100%. Coking also occurs at high C/N ratios. As already indicated, the process of this invention provides monomethylamine in substantial amounts, while minimizing the formation of dimethylamine and, especially, trimethylamine. A C/N ratio of about 1 is desirable in the process of the invention to maximize the amount of monomethylamine formed.

The efficiency of the catalyst employed herein is defined by the conversion of methanol and the selectivity to monomethylamine. As the term is used used herein, methanol conversion, assuming little or no contribution from reaction (7), in %, is 100—100 [MeOH/(MeOH+MMA+2DMA+3TMA)] and selectivity, in %, is 100 [MMA/(MMA+DMA+TMA)]. Stated in another way, conversion is determined from the amount of methanol (considered to be uncoverted) in the product mixture of methanol and the three amines. Selectivity is determined from the amount of monomethylamine relative to the monomethylamine, dimethylamine and trimethylamine in the product mixture, that is, the amount of primary amine which is produced from that portion of the methanol which has been converted. If there is significant contribution from reaction (7), conversion, in %, is 100—100 [(MMA+2DMA+3TMA)/(C/N) ratio] where MMA+DMA+TMA+NH$_3$ is 1.

A catalyst is considered non-selective herein if: (1) the observed selectivity was significantly less than that calculated (using the data of Table I and the procedures set forth at the end of Example 1) for the conventional amorphous silica-alumina catalyst, or (2) if a preponderance of unwanted TMA was produced. The relevant parameter distingluishing a selective catalyst from a non-selective catalyst is the relative adsorption (on the catalyst) of methanol vs. the three amines. Non-selective catalysts adsorb the species on the basis of their basicities: DMA>MMA>NH$_3$>MeOH; selective catalysts adsorb the species on the basis of their heats of condensation: MeOH>NH$_3$>MMA>DMA.

The following examples are provided to illustrate specific embodiments of the invention.

EXAMPLE 1

Methanol and ammonia in such amounts so as to provide C/N ratios within the ranges 0.95–1.05, that is, about 1.0, and 1.40–1.60, that is, about 1.5, were passed over 3 of sodium mordenite catalyst in a Vycor ® tubular reactor 0.5 inch (1.3 cm) in diameter and having a 3 inch (8 cm) zone heated with a split tube furnace, at atmospheric pressure, at a variety of temperatures and contact times (flow rates) within the scope of the process of the invention. The reactor effluent was analyzed by gas chromatography using a 10 foot (3 m)×0.125 inch (0.32 cm) column of polyethylene oxide (25% Carbowax ® 400), 2.5% NaOH on 80/100 mesh (U.S. Sieve Series) diatomaceous earth (Chromosorb ® WAW). The temperature was held at 65° C. for four minutes to elute the three amines and ammonia in the order: TMA, NH$_3$, DMA and MMA, and then programmed to 100° C. at 32° C./minute to elute methanol and water.

FIGS. 2 and 3 which are a part of this specification compare MMA selectivity and methanol conversion for the invention process using sodium mordenite as the catalyst and for a conventional process (carried out at atmospheric pressure except as noted, at C/N ratios within the ranges 0.90–1.10, that is, about 1.0, and 1.41–1.60, that is, about 1.5) using an amorphous silica-alumina catalyst. The points included on FIGS. 2 and 3 reflect the experimental data (shown in Tables II and III of this Example and Table VI of Example 4) which were obtained by carrying out the aforesaid procedures at the respective C/N ratios of about 1.0 and about 1.5. The curves depicted in FIGS. 2 and 3 were formulated from calculations using the parameters outlined in Table I according to the procedures set forth at the end of this example. It can be seen that there is good agreement between the experimental data and the calculated curves. The deviation (scattering) of the points (experimental data) from the curves (calculated data) represents variances in the reaction conditions as they relate to temperature, contact time, pressure and analytical measurement errors and the neglect of the amine hydrolytic reaction, that is, the reverse of reactions (1)—(3) of Table I. The figures demonstrate that the invention process using sodium mordenite catalyst, at each C/N ratio, is vastly superior to the conventional process at all levels of methanol conversion in the practical operating range of 15–95%.

PROCEDURE FOR OBTAINING CALCULATED SELECTIVITIES

The basis for the calculation is the set of relative rate constants given in Table I. These rate constants were obtained by visually fitting theoretical reaction profiles, derived as explained below, to experimental data such as given in FIGS. 2 and 3. In addition to data obtained from starting with various ratios of methanol and ammonia, the rate constants also fit data equilibrating pure or mixed amines in the absence of methanol, and three component feeds which simulate a recycle of unwanted amines to the methanol-amine reactor.

The kinetic model involves nine equations: three methanol-amine synthesis reactions, three amine equilibration reactions, and their reverses. The three methanol-amine reaction rate constants are obtained by fitting the methanol-ammonia reaction data at low and medium methanol conversions, where amine disproportionations are negligible. The three forward equilibrium. reaction rate constants are obtained from monomethylamine disproportionation data. Their reverses are obtained from thermodynamic data at 400° C. This method introduces only a minor error when reaction profiles at other temperatures are considered. The relationship between the two sets of rate constants is best obtained from the high conversion portion of the methanol-ammonia reaction.

Given the nine rate constants, the evolution of an initial methanol-ammonia reaction mixture under the influence of the catalyst can be calculated. These calculations have been performed for the standard silica-alumina catalyst at three different C/N ratios and have included consideration of the monomethylamine selectivity at three different methanol conversions. From these nine points a second-order regression equation for monomethylamine selectivity in terms of C/N ratio and methanol conversion was developed. This equation was used to calculate the expected MMA selectivity for the conventional silica-alumina catalyst as a function of C/N ratio and methanol conversion to which the observed MMA selectivities of the catalyst of the invention process are compared.

TABLE II

| Temp (°C.) | Contact Time (sec) | C/N Ratio | MeOH Conv. | STY g/g/hr | MMA Selectivity |
|---|---|---|---|---|---|
| Sodium Mordenite Catalyst | | | | | |
| 394 | 1.18 | 1.05 | 22 | 0.202 | 99 |
| 350 | 0.69 | 1.05 | 24 | 0.367 | 87 |
| 356 | 1.08 | 1.05 | 24 | 0.190 | 95 |
| 398 | 0.98 | 1.00 | 24 | 0.252 | 87 |
| 274 | 3.68 | 1.02 | 25 | 0.073 | 88 |
| 398 | 0.95 | 0.98 | 25 | 0.254 | 87 |
| 328 | 0.78 | 0.96 | 28 | 0.141 | 89 |
| 300 | 1.55 | 1.01 | 28 | 0.207 | 87 |
| 399 | 0.82 | 1.03 | 30 | 0.328 | 89 |
| 350 | 1.36 | 0.99 | 31 | 0.243 | 95 |
| 274 | 3.48 | 1.02 | 38 | 0.110 | 83 |
| 400 | 2.03 | 1.00 | 43 | 0.216 | 81 |
| 330 | 1.49 | 0.96 | 47 | 0.316 | 75 |
| 330 | 1.06 | 1.02 | 48 | 0.344 | 77 |
| 400 | 0.99 | 0.99 | 49 | 0.349 | 87 |
| 340 | 1.45 | 1.04 | 52 | 0.370 | 73 |
| 300 | 0.59 | 1.04 | 52 | 0.494 | 81 |
| 358 | 1.46 | 0.95 | 53 | 0.330 | 80 |
| 325 | 1.24 | 1.05 | 56 | 0.567 | 57 |
| 400 | 1.94 | 0.98 | 66 | 0.300 | 77 |
| 350 | 1.42 | 0.97 | 66 | 0.150 | 47 |
| 375 | 1.43 | 0.95 | 67 | 0.440 | 74 |
| 400 | 0.54 | 1.04 | 68 | 0.616 | 68 |
| 350 | 1.83 | 0.96 | 69 | 0.298 | 71 |
| 351 | 1.63 | 0.97 | 71 | 0.472 | 71 |
| 325 | 1.52 | 0.95 | 74 | 0.486 | 64 |
| 350 | 1.47 | 0.95 | 75 | 0.495 | 62 |
| 350 | 2.24 | 1.01 | 76 | 0.338 | 61 |
| 400 | 1.94 | 1.05 | 82 | 0.370 | 58 |
| 400 | 1.72 | 1.03 | 82 | 0.199 | 47 |
| 350 | 2.10 | 1.04 | 84 | 0.382 | 63 |
| 400 | 1.13 | 0.97 | 89 | 0.198 | 47 |
| Amorphous Silica-Alumina Catalyst | | | | | |
| 349 | 0.62 | 1.00 | 23 | 0.364 | 46 |
| 287 | 4.77 | 0.90 | 24 | 0.048 | 36 |
| 349 | 0.61 | 0.96 | 25 | 0.379 | 46 |
| 310 | 4.34 | 1.09 | 37 | 0.087 | 25 |
| 348* | 0.64 | 0.97 | 41 | 0.613 | 32 |
| 350* | 0.66 | 1.03 | 45 | 0.717 | 40 |
| 354** | 0.73 | 1.05 | 54 | 0.860 | 32 |
| 352** | 0.72 | 1.05 | 56 | 0.894 | 33 |
| 331 | 3.56 | 1.08 | 56 | 0.128 | 20 |
| 398 | 0.58 | 1.03 | 57 | 0.95 | 35 |
| 399 | 0.57 | 1.05 | 66 | 1.062 | 35 |
| 250 | 2.17 | 1.09 | 68 | 0.427 | 4 |
| 250 | 2.66 | 1.05 | 71 | 0.430 | 7 |
| 383 | 2.24 | 1.05 | 71 | 0.350 | 25 |
| 350 | 5.02 | 1.07 | 76 | 0.169 | 15 |
| 399*** | 0.75 | 1.10 | 80 | 1.334 | 27 |
| 399*** | 0.72 | 1.09 | 81 | 1.329 | 26 |
| 383 | 2.69 | 0.91 | 84 | 0.339 | 30 |
| 394 | 2.70 | 1.02 | 88 | 0.398 | 20 |
| 374 | 5.80 | 0.96 | 90 | 0.183 | 22 |
| 400 | 3.98 | 1.10 | 94 | 0.327 | 19 |

*at 40 psi (280 kPa)
**at 75 psi (525 kPa)
***at 42 psi (294 kPa)

TABLE III

| Temp (°C.) | Contact Time (sec) | C/N Ratio | MeOH Conv. | STY g/g/hr | MMA Selectivity |
|---|---|---|---|---|---|
| Sodium Mordenite Catalyst | | | | | |
| 300 | 1.33 | 1.46 | 20 | 0.217 | 88 |
| 347 | 0.76 | 1.45 | 23 | 0.220 | 75 |
| 347 | 0.72 | 1.58 | 24 | 0.251 | 79 |
| 300 | 2.31 | 1.54 | 24 | 0.130 | 81 |
| 347 | 0.73 | 1.57 | 24 | 0.253 | 78 |
| 347 | 0.74 | 1.60 | 25 | 0.268 | 79 |
| 347 | 0.77 | 1.58 | 25 | 0.269 | 78 |
| 347 | 0.77 | 1.59 | 26 | 0.274 | 78 |
| 345 | 0.73 | 1.44 | 26 | 0.248 | 79 |
| 328 | 0.90 | 1.42 | 29 | 0.205 | 80 |
| 250 | 15.56* | 1.47 | 29 | 0.025 | 83 |
| 399 | 1.54 | 1.58 | 31 | 0.127 | 84 |
| 400 | 1.46 | 1.44 | 32 | 0.243 | 72 |
| 350 | 1.48 | 1.45 | 32 | 0.227 | 74 |
| 402 | 0.35 | 1.47 | 33 | 0.965 | 73 |
| 333 | 1.01 | 1.50 | 36 | 0.454 | 78 |
| 420 | 1.41 | 1.42 | 37 | 0.281 | 70 |
| 325 | 1.33 | 1.43 | 39 | 0.406 | 79 |
| 450 | 1.15 | 1.60 | 41 | 0.343 | 65 |
| 377 | 1.66 | 1.48 | 44 | 0.262 | 71 |
| 350 | 0.96 | 1.40 | 45 | 0.425 | 72 |
| 400 | 1.00 | 1.50 | 46 | 0.525 | 88 |
| 350 | 1.63 | 1.58 | 46 | 0.346 | 82 |
| 400 | 0.95 | 1.52 | 47 | 0.482 | 68 |
| 400 | 0.69 | 1.46 | 49 | 0.690 | 65 |
| 350 | 1.34 | 1.47 | 52 | 0.560 | 79 |
| 450 | 0.86 | 1.60 | 55 | 0.601 | 58 |
| 450 | 1.81 | 1.40 | 59 | 0.273 | 61 |
| 400 | 1.32 | 1.53 | 63 | 0.422 | 62 |
| 400 | 2.01 | 1.43 | 66 | 0.335 | 71 |
| 400 | 1.15 | 1.42 | 71 | 0.686 | 59 |
| 475 | 0.77 | 1.53 | 74 | 0.737 | 46 |
| 372 | 5.80 | 1.52 | 75 | 0.160 | 62 |
| 400 | 0.99 | 1.43 | 76 | 0.729 | 54 |
| 425 | 1.39 | 1.60 | 78 | 0.521 | 45 |
| 350 | 2.01 | 1.43 | 80 | 0.485 | 53 |
| 399 | 5.49 | 1.40 | 80 | 0.147 | 38 |
| 425 | 0.93 | 1.52 | 80 | 0.799 | 47 |
| 400 | 1.74 | 1.48 | 82 | 0.515 | 53 |
| 375 | 2.94 | 1.40 | 83 | 0.316 | 53 |
| 400 | 1.42 | 1.43 | 85 | 0.560 | 41 |
| 350 | 6.23 | 1.41 | 87 | 0.167 | 52 |
| 400 | 0.95 | 1.54 | 87 | 0.839 | 28 |
| 400 | 1.02 | 1.47 | 91 | 0.844 | 28 |
| Amorphous Silica-Alumina Catalyst | | | | | |
| 307 | 3.35 | 1.60 | 22 | 0.091 | 25 |
| 317 | 2.67 | 1.49 | 27 | 0.103 | 24 |
| 346 | 1.04 | 1.41 | 48 | 0.469 | 7 |
| 347 | 1.93 | 1.50 | 53 | 0.203 | 22 |
| 356 | 3.71 | 1.57 | 58 | 0.227 | 14 |
| 400 | 1.07 | 1.45 | 84 | 0.751 | 19 |
| 404 | 2.32 | 1.53 | 87 | 0.636 | 10 |

*more than 3 g of catalyst used; therefore, lower rate of flow and longer contact time

EXAMPLE 2

In a manner similar to that described in Example 1, methanol and ammonia were reacted at atmospheric pressure over selected crystalline aluminosilicates (other than sodium mordenite) of the process of the invention at C/N ratios in the range 0.55 to 1.5; 3 g of catalyst was employed and the temperature was within the range 250°–458° C., contact time were 0.2–4.0 seconds (0.6–12.5 g of of methanol/g of catalyst/hour). These and control runs using various conventional (nonselective) catalysts run under substantially similar conditions for comparison are listed in Table IV. In the table, STY refers to space-time-yield, that is, grams of amines produced/gram of catalyst/hour.

TABLE IV

| Catalyst | Temp (°C.) | Contact Time (sec) | C/N Ratio | MeOH Conv. | NH₃ | Amines (Distribution) MMA | DMA | TMA | STY g/g/hr | Selectivity Observed | Calcd (as in Ex. 1) for Amorph. Silica-alumina Catalyst |
|---|---|---|---|---|---|---|---|---|---|---|---|
| Clinoptilolite Ore | 350 | 1.4 | 0.97 | 38 | 78 | 11 | 7 | 4 | 0.244 | 51 | 40 |
| Ferrierite Ore | 314 | 2.1 | 0.95 | 29 | 80 | 13 | 7 | 0 | 0.131 | 63 | 48 |
|  | 335 | 2.0 | 1.08 | 34 | 76 | 14 | 10 | 1 | 0.166 | 55 | 41 |
|  | 355 | 4.0 | 0.95 | 42 | 74 | 14 | 12 | 1 | 0.091 | 53 | 37 |
|  | 356 | 1.9 | 1.05 | 28 | 80 | 12 | 8 | 0 | 0.136 | 58 | 48 |
|  | 358 | 2.3 | 1.01 | 57 | 57 | 28 | 13 | 1 | 0.277 | 66 | 26 |
|  | 375 | 1.1 | 1.35 | 30 | 73 | 15 | 11 | 1 | 0.274 | 56 | 40 |
|  | 378 | 1.9 | 1.00 | 56 | 64 | 17 | 16 | 2 | 0.252 | 48 | 27 |
|  | 381 | 3.8 | 0.91 | 62 | 63 | 19 | 16 | 2 | 0.128 | 52 | 27 |
|  | 399 | 3.9 | 0.85 | 76 | 59 | 21 | 18 | 3 | 0.145 | 50 | 26 |
|  | 400 | 1.1 | 1.35 | 69 | 46 | 21 | 28 | 6 | 0.598 | 39 | 17 |
|  | 400 | 1.0 | 1.45 | 53 | 53 | 21 | 22 | 4 | 0.504 | 44 | 21 |
|  | 401 | 2.0 | 1.06 | 63 | 58 | 21 | 19 | 3 | 0.303 | 49 | 23 |
|  | 422 | 2.5 | 1.03 | 76 | 51 | 26 | 17 | 6 | 0.356 | 54 | 22 |
|  | 422 | 3.4 | 0.85 | 83 | 56 | 22 | 18 | 4 | 0.158 | 49 | 27 |
|  | 425 | 1.1 | 1.32 | 72 | 42 | 28 | 24 | 6 | 0.625 | 48 | 17 |
|  | 437 | 1.8 | 0.94 | 77 | 53 | 24 | 20 | 3 | 0.330 | 51 | 24 |
|  | 458 | 1.7 | 0.93 | 81 | 53 | 24 | 19 | 5 | 0.339 | 51 | 24 |
| Ca Ferrierite | 300 | 1.9 | 1.26 | 33 | 72 | 15 | 12 | 1 | 0.178 | 54 | 39 |
|  | 302 | 1.7 | 0.74 | 29 | 84 | 11 | 5 | 0 | 0.142 | 70 | 54 |
|  | 325 | 2.0 | 1.18 | 29 | 77 | 13 | 9 | 1 | 0.150 | 56 | 44 |
|  | 326 | 1.6 | 0.80 | 39 | 76 | 18 | 6 | 0 | 0.212 | 75 | 43 |
|  | 340 | 1.7 | 0.80 | 39 | 76 | 20 | 4 | 0 | 0.201 | 85 | 47 |
|  | 350 | 2.0 | 1.19 | 64 | 54 | 21 | 22 | 4 | 0.315 | 44 | 20 |
|  | 352 | 1.5 | 0.82 | 50 | 69 | 22 | 8 | 1 | 0.278 | 71 | 35 |
|  | 375 | 1.9 | 1.27 | 77 | 45 | 21 | 26 | 9 | 0.397 | 38 | 17 |
|  | 375 | 0.8 | 1.40 | 33 | 70 | 16 | 13 | 2 | 0.393 | 52 | 36 |
|  | 375 | 1.5 | 0.73 | 69 | 64 | 23 | 11 | 2 | 0.335 | 64 | 30 |
|  | 400 | 0.3 | 1.37 | 42 | 65 | 16 | 17 | 3 | 1.443 | 45 | 30 |
|  | 400 | 1.9 | 1.20 | 83 | 44 | 22 | 24 | 10 | 0.407 | 40 | 19 |
|  | 400 | 1.5 | 0.71 | 76 | 63 | 23 | 12 | 2 | 0.354 | 61 | 30 |
|  | 400 | 2.1 | 0.96 | 80 | 54 | 21 | 19 | 6 | 0.321 | 45 | 24 |
|  | 408 | 1.1 | 1.25 | 40 | 64 | 26 | 9 | 2 | 0.335 | 70 | 33 |
|  | 408 | 1.4 | 0.80 | 21 | 70 | 21 | 7 | 2 | 0.276 | 70 | 35 |
|  | 408 | 1.5 | 0.76 | 71 | 63 | 23 | 10 | 3 | 0.354 | 63 | 29 |
|  | 425 | 0.2 | 1.43 | 42 | 61 | 18 | 17 | 4 | 1.605 | 47 | 26 |
|  | 425 | 1.8 | 1.13 | 86 | 45 | 23 | 20 | 12 | 0.403 | 42 | 21 |
|  | 450 | 0.2 | 1.48 | 43 | 63 | 18 | 16 | 3 | 1.503 | 47 | 29 |
|  | 450 | 0.3 | 1.36 | 47 | 61 | 18 | 17 | 4 | 1.605 | 47 | 26 |
| Fe Fer. | 400 | 1.8 | 0.87 | 66 | 67 | 16 | 10 | 7 | 0.240 | 48 | 27 |
| Sr Fer. | 400 | 1.7 | 1.23 | 73 | 47 | 25 | 20 | 8 | 0.373 | 47 | 18 |
| K Fer. | 400 | 1.8 | 1.13 | 72 | 52 | 21 | 19 | 7 | 0.338 | 45 | 20 |
| Li Fer. | 400 | 2.1 | 0.91 | 81 | 55 | 21 | 19 | 5 | 0.309 | 46 | 25 |
| Ba Fer. | 400 | 2.1 | 0.88 | 80 | 58 | 21 | 15 | 7 | 0.295 | 49 | 26 |
| Ce Fer. | 400 | 1.8 | 1.14 | 69 | 55 | 19 | 19 | 7 | 0.322 | 43 | 20 |
| Erionite ore | 300 | 1.6 | 0.78 | 39 | 80 | 12 | 7 | 2 | 0.196 | 58 | 44 |
|  | 400 | 1.2 | 1.26 | 87 | 46 | 17 | 19 | 18 | 0.668 | 31 | 19 |
| Ca Erionite | 300 | 1.7 | 0.98 | 35 | 78 | 12 | 7 | 3 | 0.218 | 55 | 42 |
|  | 300 | 1.8 | 0.97 | 41 | 76 | 13 | 8 | 4 | 0.253 | 52 | 37 |
|  | 325 | 1.2 | 1.29 | 37 | 71 | 15 | 10 | 5 | 0.304 | 51 | 34 |
|  | 350 | 1.2 | 1.42 | 49 | 60 | 17 | 15 | 8 | 0.434 | 43 | 24 |
|  | 350 | 1.7 | 1.08 | 60 | 63 | 16 | 14 | 7 | 0.399 | 44 | 24 |
|  | 350 | 1.8 | 1.12 | 84 | 54 | 15 | 16 | 16 | 0.565 | 32 | 21 |
|  | 357 | 1.7 | 1.03 | 84 | 56 | 15 | 15 | 14 | 0.524 | 34 | 23 |
|  | 359 | 1.6 | 1.12 | 55 | 63 | 17 | 14 | 6 | 0.388 | 47 | 25 |
|  | 375 | 1.5 | 1.12 | 74 | 55 | 18 | 18 | 10 | 0.508 | 39 | 20 |
|  | 383 | 0.8 | 1.33 | 62 | 54 | 19 | 18 | 9 | 0.506 | 42 | 19 |
|  | 400 | 1.2 | 1.42 | 81 | 43 | 18 | 21 | 18 | 0.689 | 31 | 15 |
|  | 400 | 1.4 | 1.19 | 89 | 49 | 15 | 17 | 19 | 0.635 | 29 | 20 |
|  | 422 | 1.0 | 1.34 | 91 | 44 | 15 | 16 | 25 | 0.727 | 27 | 18 |
|  | 425 | 1.3 | 1.33 | 93 | 42 | 17 | 19 | 23 | 0.736 | 28 | 19 |
|  | 425 | 2.5 | 1.40 | 94 | 42 | 14 | 16 | 28 | 0.455 | 24 | 18 |
| Ca Mord. | 250 | 1.7 | 0.70 | 75 | 66 | 19 | 11 | 4 | 0.340 | 55 | 31 |
|  | 275 | 2.0 | 0.57 | 51 | 74 | 22 | 3 | 0 | 0.213 | 87 | 41 |
|  | 275 | 1.4 | 0.88 | 79 | 54 | 26 | 15 | 5 | 0.454 | 58 | 26 |
|  | 275 | 2.1 | 1.04 | 47 | 60 | 31 | 8 | 1 | 0.228 | 79 | 31 |
|  | 275 | 2.2 | 1.22 | 32 | 67 | 28 | 6 | 0 | 0.186 | 83 | 40 |
|  | 300 | 1.4 | 1.22 | 43 | 57 | 33 | 9 | 0 | 0.377 | 77 | 34 |
|  | 300 | 1.5 | 1.02 | 40 | 68 | 24 | 7 | 0 | 0.281 | 76 | 37 |
|  | 300 | 1.6 | 0.96 | 51 | 60 | 31 | 8 | 1 | 0.344 | 78 | 31 |
|  | 300 | 1.3 | 1.08 | 86 | 45 | 28 | 18 | 10 | 0.589 | 50 | 22 |

TABLE IV-continued

| Catalyst | Temp (°C.) | Contact Time (sec) | C/N Ratio | MeOH Conv. | Amines (Distribution) NH₃ | MMA | DMA | TMA | STY g/g/hr | Selectivity Observed | Calcd (as in Ex. 1) for Amorph. Silica-alumina Catalyst |
|---|---|---|---|---|---|---|---|---|---|---|---|
| | 300 | 1.2 | 1.15 | 36 | 65 | 29 | 6 | 0 | 0.356 | 82 | 38 |
| | 300 | 2.0 | 1.30 | 51 | 49 | 37 | 13 | 1 | 0.302 | 72 | 24 |
| | 325 | 1.8 | 0.61 | 89 | 61 | 26 | 12 | 2 | 0.363 | 65 | 35 |
| | 325 | 1.6 | 1.06 | 93 | 46 | 24 | 18 | 13 | 0.611 | 43 | 24 |
| | 325 | 2.0 | 1.06 | 83 | 42 | 33 | 20 | 5 | 0.376 | 56 | 22 |
| | 325 | 2.0 | 1.18 | 57 | 49 | 37 | 13 | 2 | 0.303 | 72 | 23 |
| | 350 | 1.7 | 0.69 | 94 | 57 | 22 | 15 | 4 | 0.417 | 54 | 34 |
| Ca Mord. | 350 | 1.1 | 1.13 | 72 | 43 | 37 | 18 | 3 | 0.652 | 63 | 20 |
| | 350 | 2.0 | 1.23 | 86 | 35 | 33 | 23 | 9 | 0.446 | 51 | 19 |
| | 350 | 0.3 | 1.47 | 44 | 55 | 28 | 15 | 2 | 1.685 | 63 | 27 |
| | 354 | 1.5 | 0.88 | 88 | 51 | 26 | 18 | 5 | 0.488 | 54 | 27 |
| | 356 | 1.4 | 0.98 | 87 | 44 | 30 | 21 | 4 | 0.544 | 54 | 24 |
| | 375 | 1.2 | 1.01 | 90 | 44 | 29 | 21 | 7 | 0.702 | 50 | 25 |
| | 375 | 1.8 | 1.15 | 89 | 40 | 27 | 24 | 9 | 0.425 | 45 | 21 |
| | 410 | 1.3 | 0.95 | 93 | 48 | 25 | 19 | 9 | 0.549 | 47 | 27 |
| | 450 | 0.2 | 1.49 | 77 | 38 | 25 | 21 | 16 | 0.812 | 41 | 14 |
| | 457 | 1.3 | 0.80 | 62 | 64 | 26 | 6 | 4 | 0.338 | 72 | 30 |
| Sr Mord. | 400 | 1.63 | 1.40 | 93 | 34 | 20 | 27 | 19 | 0.524 | 30 | 18 |
| Zn Mord. | 400 | 1.15 | 1.09 | 28 | 83 | 9 | 4 | 4 | 0.125 | 50 | 47 |
| K Mord. | 400 | 1.34 | 1.34 | 26 | 77 | 13 | 7 | 3 | 0.151 | 57 | 45 |
| Ba Mord. | 324 | 1.75 | 1.22 | 39 | 61 | 33 | 7 | 1 | 0.262 | 82 | 34 |
| | 345 | 1.66 | 1.12 | 59 | 48 | 40 | 12 | 1 | 0.358 | 76 | 23 |
| | 365 | 1.68 | 1.06 | 76 | 40 | 41 | 16 | 3 | 0.427 | 68 | 21 |
| | 377 | 1.64 | 1.07 | 39 | 66 | 27 | 6 | 1 | 0.232 | 80 | 36 |
| | 385 | 1.64 | 1.08 | 82 | 41 | 35 | 20 | 5 | 0.451 | 59 | 21 |
| | 396 | 1.59 | 1.05 | 56 | 56 | 32 | 9 | 3 | 0.313 | 73 | 26 |
| | 400 | 0.26 | 1.42 | 26 | 73 | 19 | 7 | 1 | 0.997 | 69 | 44 |
| | 406 | 1.60 | 0.97 | 89 | 45 | 29 | 19 | 7 | 0.434 | 54 | 25 |
| | 419 | 1.53 | 0.97 | 77 | 51 | 20 | 13 | 6 | 0.382 | 61 | 23 |
| | 425 | 1.60 | 0.88 | 87 | 54 | 23 | 15 | 8 | 0.381 | 51 | 27 |
| Natural Mord. Ore | 400 | 1.96 | 1.16 | 89 | 45 | 24 | 15 | 17 | 0.639 | 44 | 21 |
| | 402 | 1.42 | 1.19 | 91 | 48 | 16 | 16 | 20 | 0.650 | 32 | 21 |
| Cr Mord. | 400 | 1.94 | 0.84 | 92 | 61 | 15 | 10 | 14 | 0.316 | 38 | 30 |
| Li Mord. | 403 | 3.40 | 0.94 | 26 | 82 | 14 | 2 | 2 | 0.065 | 78 | 52 |
| NaH Mord. | 330 | 1.20 | 0.97 | 38 | 69 | 25 | 6 | 0 | 0.185 | 80 | 40 |
| (4.2% Na) | 330 | 1.25 | 0.97 | 29 | 75 | 23 | 3 | 0 | 0.209 | 88 | 48 |
| | 330 | 1.21 | 0.96 | 28 | 76 | 21 | 3 | 0 | 0.193 | 88 | 50 |
| | 330 | 1.25 | 1.03 | 36 | 69 | 25 | 6 | 0 | 0.187 | 81 | 40 |
| | 330 | 1.18 | 0.71 | 36 | 77 | 20 | 3 | 0 | 0.265 | 89 | 48 |
| | 330 | 1.19 | 0.86 | 36 | 73 | 24 | 4 | 0 | 0.324 | 86 | 44 |
| | 330 | 1.08 | 0.85 | 46 | 68 | 26 | 7 | 0 | 0.274 | 79 | 37 |
| CONTROL EXAMPLES (Conventional Catalysts) | | | | | | | | | | | |
| Ca-Na-A Zeolite | 400 | 1.2 | 1.47 | 95 | 38 | 17 | 14 | 32 | 0.871 | 27 | 18 |
| | 300 | 2.2 | 1.25 | 80 | 58 | 10 | 7 | 25 | 0.394 | 24 | 18 |
| Silica-Alumina | 400 | 1.0 | 1.45 | 84 | 51 | 9 | 7 | 33 | 0.751 | 19 | 15 |
| | 347 | 1.9 | 1.50 | 53 | 68 | 7 | 3 | 23 | 0.203 | 22 | 20 |
| K-Na-A Zeolite | 400 | 1.0 | 1.24 | 55 | 65 | 13 | 10 | 12 | 0.438 | 36 | 23 |
| Na-Y Zeolite | 400 | 0.9 | 1.45 | 90 | 43 | 14 | 12 | 31 | 0.818 | 24 | 17 |
| | 300 | 2.3 | 1.02 | 38 | 86 | 1 | 1 | 12 | 0.148 | 7 | 39 |
| Ca-X Zeolite | 400 | 1.0 | 1.24 | 93 | 48 | 14 | 13 | 25 | 0.721 | 26 | 21 |
| Na-X Zeolite | 400 | 0.8 | 1.36 | 84 | 55 | 7 | 6 | 31 | 0.699 | 16 | 43 |
| | 300 | 2.2 | 1.19 | 65 | 73 | 1 | 0 | 25 | 0.298 | 4 | 20 |
| Hydrogen Mordenite | 300 | 2.0 | 1.50 | 69 | 64 | 2 | 2 | 33 | 0.399 | 5 | 15 |
| | 265 | 1.0 | 1.30 | 53 | 66 | 13 | 6 | 15 | 0.604 | 39 | 23 |
| γ-Al₂O₃ | 346 | 4.0 | 1.19 | 84 | 59 | 9 | 7 | 26 | 0.252 | 21 | 19 |
| | 328 | 4.0 | 1.21 | 91 | 56 | 8 | 7 | 29 | 0.278 | 18 | 21 |
| Rare Earth-X Zeolite | 273 | 1.8 | 1.04 | 39 | 86 | 1 | 0 | 13 | 0.238 | 6 | 37 |
| | 300 | 1.0 | 1.10 | 83 | 68 | 2 | 3 | 28 | 1.126 | 6 | 21 |
| | 319 | 0.8 | 1.06 | 94 | 61 | 4 | 9 | 26 | 1.558 | 11 | 25 |
| | 332 | 1.8 | 1.22 | 89 | 55 | 9 | 10 | 27 | 0.637 | 19 | 20 |
| Na ZSM-8 Zeolite | 298 | 2.2 | 1.09 | 78 | 67 | 3 | 8 | 22 | 0.492 | 9 | 21 |
| HZSM-5 Zeolite | 268 | 1.9 | 1.03 | 45 | 84 | 1 | 1 | 15 | 0.250 | 4 | 33 |
| | 290 | 2.1 | 1.00 | 81 | 72 | 1 | 2 | 25 | 0.434 | 4 | 23 |
| | 327 | 2.1 | 1.02 | 99 | 60 | 8 | 8 | 23 | 0.516 | 21 | 25 |
| NaZSM-5 Zeolite | 337 | 1.4 | 1.11 | 40 | 83 | 2 | 3 | 12 | 0.279 | 14 | 35 |
| | 359 | 1.5 | 0.99 | 63 | 77 | 2 | 3 | 18 | 0.385 | 8 | 25 |
| | 397 | 1.5 | 1.04 | 93 | 59 | 11 | 11 | 21 | 0.615 | 25 | 25 |

TABLE IV-continued

| Catalyst | Temp (°C.) | Contact Time (sec) | C/N Ratio | MeOH Conv. | Amines (Distribution) | | | | STY g/g/hr | Selectivity Observed | Calcd (as in Ex. 1) for Amorph. Silica-alumina Catalyst |
|---|---|---|---|---|---|---|---|---|---|---|---|
| | | | | | NH₃ | MMA | DMA | TMA | | | |
| Chabazite | 350 | 1.5 | 1.14 | 93 | 52 | 13 | 13 | 22 | 0.629 | 26 | 22 |

EXAMPLE 3

In this example, the preferred catalyst for MMA selectivity, sodium mordenite, was utilized in two runs conducted under elevated pressure. An equimolar mixture of methanol and ammonia was passed at a rate of 22 mmole/minute over sodium mordenite (11.5 g) contained in a 0.5 inch (1.3 cm), outer diameter, ×9 inch (23 cm) tubular reactor. A Grove® valve was used to regulate the reaction pressure and temperature was maintained at 400° C. by immersion of the reactor in a sand bath. Table V summarizes the experimental data obtained. The contact time is the time at the indicated pressure; the STY is the space-time-yield in g of product/gram of catalyst/hour.

TABLE V

| Contact Time (sec) | Pressure (psig (kPa)) | STY MMA | STY DMA | STY TMA | STY Amines | MeOH Conv | MMA Selec |
|---|---|---|---|---|---|---|---|
| 7.2 | 100 (700) | 353 | 44 | 22 | .419 | 19 | 90 |
| 21.6 | 300 (2000) | 270 | 42 | 24 | .336 | 24 | 88 |

EXAMPLE 4

In a manner similar to that described in Example 3, except that the tubular reactor was 0.125 inch (0.32 cm)×6 inches (15.2 cm), methanol and ammonia were reacted over 3 g of sodium mordenite or calcium ferrierite at various C/N ratios, temperatures, pressures and contact times. The data for these runs are tabulated in Tables VI (for sodium mordenite) and VII (for calcium ferrierite).

TABLE VI

| Pressure (psig (kPa)) | Temp (°C.) | Contact Time (sec) at 1 atm | C/N Ratio | MeOH Conv. | Amines (Distribution) | | | | STY g/g/hr | MMA Selectivity |
|---|---|---|---|---|---|---|---|---|---|---|
| | | | | | NH₃ | MMA | DMA | TMA | | |
| 10 (70) | 336 | 1.1 | 1.00 | 35 | 73 | 22 | 6 | 0 | 0.334 | 85 |
| 20 (140) | 394 | 1.3 | 0.84 | 28 | 78 | 20 | 2 | 0 | 0.213 | 91 |
| 28 (190) | 399 | 1.0 | 0.96 | 22 | 83 | 15 | 2 | 0 | 0.199 | 88 |
| 40 (280) | 334 | 1.3 | 0.86 | 43 | 69 | 26 | 5 | 0 | 0.374 | 84 |
| 44 (300) | 325 | 1.1 | 0.54 | 27 | 89 | 9 | 2 | 1 | 0.197 | 75 |
| 46 (320) | 326 | 1.0 | 0.74 | 38 | 78 | 16 | 6 | 0 | 0.375 | 73 |
| 46 (320) | 394 | 1.5 | 0.66 | 51 | 70 | 27 | 3 | 0 | 0.295 | 90 |
| 59 (410) | 393 | 1.6 | 0.47 | 58 | 76 | 21 | 2 | 0 | 0.202 | 91 |
| 61 (420) | 393 | 1.3 | 0.84 | 36 | 74 | 24 | 3 | 0 | 0.263 | 89 |
| 70 (480) | 399 | 1.5 | 1.58 | 32 | 58 | 35 | 6 | 1 | 0.127 | 83 |
| 70 (480) | 399 | 3.9 | 0.84 | 52 | 66 | 27 | 5 | 1 | 0.105 | 82 |
| 70 (480) | 399 | 4.0 | 0.80 | 55 | 67 | 26 | 5 | 1 | 0.102 | 81 |
| 72 (500) | 400 | 1.0 | 0.98 | 26 | 80 | 18 | 2 | 1 | 0.248 | 86 |
| 72 (500) | 400 | 1.7 | 1.02 | 36 | 70 | 28 | 0 | 2 | 0.180 | 93 |
| 72 (500) | 400 | 1.1 | 0.77 | 40 | 74 | 22 | 3 | 1 | 0.311 | 88 |
| 72 (500) | 400 | 1.0 | 0.93 | 31 | 76 | 20 | 6 | 0 | 0.322 | 77 |
| 72 (500) | 400 | 1.1 | 0.92 | 20 | 85 | 14 | 1 | 0 | 0.184 | 93 |
| 72 (500) | 400 | 2.0 | 1.00 | 45 | 65 | 29 | 5 | 1 | 0.217 | 83 |
| 72 (500) | 400 | 1.1 | 0.77 | 48 | 70 | 25 | 5 | 1 | 0.368 | 81 |
| 72 (500) | 400 | 1.2 | 0.87 | 51 | 67 | 27 | 6 | 1 | 0.414 | 79 |
| 72 (500) | 400 | 1.1 | 1.10 | 57 | 57 | 31 | 9 | 3 | 0.552 | 72 |
| 74 (510) | 425 | 2.0 | 0.93 | 75 | 50 | 37 | 11 | 3 | 0.391 | 73 |
| 75 (520) | 341 | 0.9 | 1.34 | 21 | 75 | 23 | 2 | 1 | 0.177 | 88 |
| 75 (520) | 341 | 0.9 | 0.99 | 23 | 80 | 18 | 2 | 0 | 0.281 | 90 |
| 75 (520) | 341 | 0.9 | 1.37 | 27 | 72 | 23 | 5 | 1 | 0.212 | 79 |
| 75 (520) | 341 | 0.9 | 1.02 | 32 | 70 | 27 | 3 | 0 | 0.208 | 90 |
| 75 (520) | 341 | 0.9 | 1.14 | 37 | 69 | 21 | 10 | 0 | 0.339 | 68 |
| 75 (520) | 374 | 0.9 | 0.79 | 42 | 71 | 26 | 3 | 1 | 0.413 | 87 |
| 75 (520) | 373 | 0.9 | 0.72 | 45 | 72 | 25 | 3 | 0 | 0.401 | 89 |
| 75 (520) | 341 | 1.0 | 0.77 | 52 | 71 | 18 | 10 | 1 | 0.323 | 60 |
| 75 (520) | 399 | 1.1 | 0.75 | 59 | 65 | 29 | 5 | 1 | 0.514 | 83 |
| 75 (520) | 422 | 1.0 | 0.83 | 64 | 58 | 33 | 8 | 1 | 0.621 | 80 |
| 75 (520) | 398 | 1.3 | 0.78 | 69 | 53 | 43 | 4 | 1 | 0.666 | 90 |
| 75 (520) | 406 | 2.4 | 0.83 | 76 | 50 | 41 | 8 | 2 | 0.279 | 80 |
| 76 (520) | 394 | 1.5 | 0.52 | 60 | 73 | 24 | 8 | 0 | 0.270 | 89 |
| 77 (530) | 407 | 2.2 | 0.84 | 79 | 49 | 39 | 9 | 2 | 0.382 | 78 |
| 77 (530) | 408 | 2.3 | 0.79 | 76 | 53 | 38 | 8 | 2 | 0.349 | 79 |
| 77 (530) | 422 | 1.1 | 0.76 | 67 | 61 | 31 | 7 | 2 | 0.587 | 78 |
| 77 (530) | 425 | 1.2 | 1.31 | 56 | 44 | 43 | 11 | 2 | 0.424 | 77 |
| 78 (540) | 390 | 1.5 | 0.47 | 60 | 75 | 23 | 2 | 0 | 0.251 | 92 |
| 80 (550) | 399 | 0.6 | 1.19 | 30 | 69 | 28 | 3 | 1 | 0.370 | 88 |
| 80 (550) | 335 | 1.2 | 0.85 | 36 | 73 | 25 | 2 | 0 | 0.317 | 93 |

TABLE VI-continued

| Pressure (psig (kPa)) | Temp (°C.) | Contact Time (sec) at 1 atm | C/N Ratio | MeOH Conv. | Amines (Distribution) NH₃ | MMA | DMA | TMA | STY g/g/hr | MMA Selectivity |
|---|---|---|---|---|---|---|---|---|---|---|
| 80 (550) | 399 | 0.9 | 0.93 | 41 | 68 | 28 | 3 | 1 | 0.317 | 88 |
| 80 (550) | 399 | 0.9 | 0.95 | 44 | 65 | 31 | 4 | 1 | 0.413 | 89 |
| 80 (550) | 399 | 1.0 | 1.01 | 48 | 59 | 35 | 5 | 1 | 0.483 | 85 |
| 80 (550) | 399 | 1.2 | 0.87 | 60 | 56 | 38 | 6 | 1 | 0.525 | 86 |
| 95 (650) | 397 | 1.2 | 0.78 | 20 | 85 | 14 | 1 | 0 | 0.100 | 93 |
| 95 (650) | 395 | 0.8 | 0.91 | 23 | 80 | 18 | 1 | 0 | 0.191 | 95 |
| 95 (650) | 395 | 0.8 | 0.66 | 27 | 84 | 15 | 1 | 0 | 0.159 | 94 |
| 95 (650) | 392 | 0.9 | 0.91 | 24 | 79 | 20 | 1 | 0 | 0.140 | 95 |
| 97 (670) | 395 | 0.8 | 0.50 | 26 | 88 | 11 | 1 | 0 | 0.166 | 92 |
| 101 (700) | 396 | 0.8 | 0.91 | 24 | 80 | 19 | 1 | 0 | 0.197 | 95 |
| 102 (700) | 323 | 1.1 | 0.62 | 42 | 80 | 15 | 5 | 0 | 0.353 | 75 |
| 111 (760) | 326 | 1.8 | 0.56 | 52 | 78 | 15 | 7 | 0 | 0.219 | 68 |
| 115 (790) | 326 | 1.0 | 0.63 | 41 | 80 | 15 | 5 | 0 | 0.346 | 75 |
| 122 (840) | 400 | 1.6 | 0.91 | 49 | 63 | 31 | 6 | 1 | 0.345 | 82 |
| 122 (840) | 400 | 1.6 | 0.78 | 58 | 64 | 30 | 5 | 1 | 0.333 | 83 |
| 122 (840) | 400 | 1.3 | 0.81 | 61 | 63 | 29 | 7 | 1 | 0.355 | 78 |

TABLE VII

| Pressure (psig (kPa)) | Temp (°C.) | Contact Time (sec) at 1 atm | C/N Ratio | MeOH Conv. | Amines (Distribution) NH₃ | MMA | DMA | TMA | STY g/g/hr | MMA Selectivity |
|---|---|---|---|---|---|---|---|---|---|---|
| 77 (530) | 340 | 1.7 | 0.82 | 34 | 76 | 20 | 4 | 0 | 0.201 | 83 |
| 77 (530) | 370 | 1.0 | 2.17 | 26 | 55 | 35 | 9 | 1 | 0.387 | 78 |
| 77 (530) | 370 | 2.0 | 0.94 | 56 | 57 | 35 | 7 | 1 | 0.371 | 81 |
| 77 (530) | 400 | 1.1 | 0.99 | 50 | 68 | 21 | 9 | 3 | 0.306 | 64 |
| 77 (530) | 400 | 1.1 | 1.23 | 46 | 62 | 25 | 11 | 3 | 0.361 | 64 |
| 77 (530) | 426 | 1.1 | 0.94 | 56 | 68 | 21 | 7 | 4 | 0.313 | 65 |
| 77 (530) | 425 | 1.2 | 1.26 | 35 | 73 | 18 | 6 | 4 | 0.264 | 64 |
| 77 (530) | 428 | 0.7 | 0.88 | 26 | 85 | 12 | 2 | 1 | 0.263 | 80 |

EXAMPLE 5

In a manner similar to that described in Example 1, methanol and ammonia were reacted at atmospheric pressure, at 358° C., over sodium mordenite, various sodium hydrogen mordenites of the process of the invention and a sodium hydrogen mordenite and a hydrogen mordenite outside the process of the invention; 3 g of each catalyst was used. The data for these runs are tabulated in Table VIII, the last two runs being the control runs.

TABLE VIII

| Catalyst | % Na | Contact Time (sec) | C/N Ratio | MeOH Conv. | Amines (Distribution) NH₃ | MMA | DMA | TMA | STY g/g/hr | MMA Selectivity |
|---|---|---|---|---|---|---|---|---|---|---|
| Na Mordenite | 4.4 | 1.3 | 1.28 | 42 | 55 | 37 | 8 | 1 | 0.360 | 80 |
| NaH Mordenite | 4.3 | 1.4 | 1.33 | 59 | 44 | 35 | 21 | 1 | 0.460 | 61 |
| NaH Mordenite | 4.2 | 1.4 | 1.15 | 65 | 45 | 37 | 17 | 1 | 0.480 | 67 |
| NaH Mordenite | 2.7 | 1.3 | 1.13 | 56 | 44 | 19 | 20 | 17 | 0.620 | 34 |
| NaH Mordenite | 1.4 | 1.3 | 1.35 | 59 | 41 | 14 | 19 | 27 | 0.720 | 23 |
| H Mordenite | — | 1.3 | 1.40 | 98 | 41 | 14 | 33 | 33 | 0.755 | 23 |

I claim:

1. Catalytic process for producing monomethylamine from methanol and ammonia, said process comprising reacting methanol and ammonia, in such amounts so as to provide a C/N ratio, from the methanol and ammonia reactants, of 0.5-1.5, over the catalyst selected from
   (a) mordenite wherein the primary cation is Li, Na, HNa having at least 2% Na by weight, K, Ca, Sr, Ba, Ce, Zn or Cr
   (b) ferrierite wherein the primary metal cation is Li, Na, K, Ca, Sr, Ba, Ce or Fe
   (c) erionite ore
   (d) calcium erionite and
   (e) clinoptilolite ore, at a temperature of 250°-475° C., a pressure of 7-7000 kPa, a contact time, normalized to 7 kPa pressure, of 0.1-60 seconds and a methanol conversion of 15-95%.

2. Process of claim 1 wherein the temperature is 350°-400° C.

3. Process of claim 1 wherein the catalyst is sodium mordenite.

4. Process of claim 1 wherein the catalyst is hydrogen-sodium mordenite having at least 2% Na by weight.

5. Process of claim 1 which is carried out continuously.

6. Process of claim 1 wherein the pressure is 70-3000 kPa.

7. Process of claim 1 wherein the contact time, normalized to 7 kPa pressure, is 1-10 seconds.

8. Process of claim 1 wherein the C/N ratio is 0.95 to 1.05.

* * * * *